(12) United States Patent
Galloway et al.

(10) Patent No.: US 7,160,313 B2
(45) Date of Patent: Jan. 9, 2007

(54) LOAD-CONTROLLED DEVICE FOR A PATTERNED SKIN INCISION

(75) Inventors: Edward L. Galloway, Beaumont, TX (US); Eric Petersen, Beaumont, TX (US); Tipton Golias, Beaumont, TX (US)

(73) Assignee: Helena Laboratories, Beaumont, TX (US)

( * ) Notice: Subject to any disclaimer, the term of this patent is extended or adjusted under 35 U.S.C. 154(b) by 325 days.

(21) Appl. No.: 10/792,025

(22) Filed: Mar. 3, 2004

(65) Prior Publication Data

US 2005/0125018 A1    Jun. 9, 2005

Related U.S. Application Data

(63) Continuation-in-part of application No. 10/628,199, filed on Jul. 28, 2003.

(51) Int. Cl.
  *A61B 17/32* (2006.01)
  *A61B 17/14* (2006.01)
  *A61B 5/00* (2006.01)
(52) U.S. Cl. ............... 606/167; 606/181; 606/182; 600/583
(58) Field of Classification Search ........ 606/181–185, 606/167; 600/583; 604/220
  See application file for complete search history.

(56) References Cited

U.S. PATENT DOCUMENTS

| 4,064,871 | A | 12/1977 | Reno |
| 4,535,769 | A | 8/1985 | Burns |
| 4,643,189 | A | 2/1987 | Mintz |
| 5,314,441 | A * | 5/1994 | Cusack et al. ............. 606/182 |
| 5,395,388 | A | 3/1995 | Schraga |
| 5,527,333 | A | 6/1996 | Nikkels et al. |
| 5,529,581 | A * | 6/1996 | Cusack ..................... 606/181 |
| 5,584,846 | A | 12/1996 | Mawhirt et al. |
| 5,797,940 | A | 8/1998 | Mawhirt et al. |
| 5,851,215 | A | 12/1998 | Mawhirt et al. |
| 5,951,582 | A * | 9/1999 | Thorne et al. ............. 606/182 |
| 6,206,901 | B1 * | 3/2001 | Rutynowski et al. ....... 606/182 |
| 6,221,089 | B1 | 4/2001 | Mawhirt |
| 6,432,120 | B1 | 8/2002 | Teo |

\* cited by examiner

*Primary Examiner*—Glenn K. Dawson
*Assistant Examiner*—Kathleen Sonnett
(74) *Attorney, Agent, or Firm*—Egbert Law Offices

(57) ABSTRACT

A skin incision device has a casing having a bottom surface with a slot formed therein, a cover positioned on the casing and slidable in a direction toward the bottom surface, a blade positioned in the casing adjacent the slot, an actuator cooperatively positioned between the cover and an interior of the casing, and a carriage element. The actuator engages the blade by its horizontal displacement triggered by the slidable movement of the cover toward the bottom surface of the casing. The carriage element guides the movement of the blade between a pre-actuated position and a post-actuated position. The blade moves outwardly through the slot, cuts with a horizontal movement, and returns inwardly through the slot.

17 Claims, 5 Drawing Sheets

LOAD-CONTROLLED DEVICE FOR A PATTERNED SKIN INCISION

RELATED U.S. APPLICATIONS

The present application is a continuation-in-part application claiming priority from U.S. patent application Ser. No. 10/628,199, filed on Jul. 28, 2003, and entitled "LOAD-CONTROLLED AUTO-ACTUATED SKIN INCISION DEVICE", presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to medical devices. More particularly, the present invention relates to devices for incising the skin. In particular, the present invention relates to internal actuators for skin incising devices which apply a controlled load and a constant force during the incising operation for a patterned incision. Additionally, the present invention relates to skin incising devices that are used for the purpose of blood acquisition.

BACKGROUND OF THE INVENTION

In the medical field, it is a very common procedure, and often very necessary, to conduct a bleeding time test which measures the time required for the cessation of bleeding following a skin incision. This test is medically important because extended or prolonged bleeding time can be associated with, for example, a lack of or a great excess of platelets, abnormality of platelet function, coating of platelets by specific proteins or foreign materials or the action of certain drugs; e.g., aspirin.

Although the bleeding time test procedure was first described approximately ninety years ago, it did not receive general acceptance until the 1940's at which time the test's sensitivity was increased by making a skin incision on the forearm of the patient while maintaining a blood pressure cuff inflation to maintain venostasis at a standardized level. Using this procedure, a technologist simultaneously starts a stopwatch while making the incision. The emerging blood is then gently blotted every thirty seconds. The cessation of bleeding is defined as the time at which the blotting paper is no longer stained by the emerging blood. This amount of time is generally recorded to the nearest half minute.

Disposable bleeding time devices were first introduced in 1978 to facilitate automation and convenience. These devices improved the acceptance of the test by both the patient and the operator. However, the results were still subject to a variety of technical variables. Additionally, these devices were significantly more expensive than previous methods. This hindered the acceptance of such devices in many countries around the world. Importantly, different disposable devices evolved over time which were functionally quite dissimilar so that the results were not comparable. Thus, standardization remained an elusive goal in bleeding time testing.

An important bleeding time testing device is known as the TRIPLETT™ bleeding time testing device. This was named after the noted physician in blood coagulation and hematopathology, Dr. Douglas Triplett. This device is presently manufactured and sold by Helena Laboratories of Beaumont, Tex. This device met the goal of global standardization in bleeding time testing and utilizes advanced technology at a universally affordable price. This was a product that provided a new level of value to automated, disposable bleeding time devices. This TRIPLETT™ bleeding time testing device was designed to be user and patient friendly, virtually painless, and to mimic the incision motion of the original bleeding time method. The device makes a standardized surgical incision one millimeter deep by five millimeters long for accurate sensitive bleeding time testing. The blade automatically retracts after incisions so as to ensure safety. The device includes a large contact surface that distributes the downward force over a wider area of skin so as to reduce the potential for deep non-standardized cuts. This device is presently subject to patent protection under U.S. Pat. Nos. 5,662,672 and 5,733,300.

In the past, various U.S. patents have issued in association with devices for creating incisions in skin. There is a wide variety of inventions specifically geared toward creation of skin incisions for use in the medical field for blood sampling and bleeding time testing. U.S. Pat. No. 4,535,769, issued on Aug. 20, 1985 to Burns, discloses an automatic retractable lancet assembly that includes a housing with a sharp-pointed lancet movably mounted therein. A depressible plunger and slide mechanism actuates the movement of the lancet outwardly from the housing, which is an elongate cylinder.

U.S. Pat. No. 5,527,333, issued on Jun. 18, 1996 to Nikkels et al., presents a disposable blood sampling device for a precise incision of predetermined length and depth in the skin of a patient. A trigger is slidably disposed in the opening in the top surface of the device, which is generally cylindrical in shape. A single spring, only, is extended by the trigger when the device is actuated.

U.S. Pat. No. 5,529,581, issued on Jun. 25, 1996 to Cusack, also teaches a lancet device and associated method used for obtaining a blood sample from a patient. A slotted aperture is formed through a safety housing in the region of the housing placed against the skin. An invertible spring member is a curved structure that automatically inverts into a generally oppositely curved orientation when the invertible spring member is flattened by a predetermined degree. U.S. Pat. No. 5,797,940, issued on Aug. 25, 1998 to Mawhirt et al., describes a device for making an adjustably sized incision in skin. The device comprises a housing having a slotted opening; a blade; a triggering mechanism and an incision size adjusting mechanism associated with the housing for selectively adjusting the size of the incision.

U.S. Pat. No. 5,395,388, issued on Mar. 7, 1995 to Schraga, describes a single use disposable lancet device including a generally cylindrical housing wherein a spring is contained, the spring including a first end fixed within the housing and having a movable second end zone with a pointed blade or terminal end, the second end zone being movable relative to a normal position with the pointed terminal end contained within the housing and adjacent a first opening in the housing.

A study of the prior art also reveals a number of low-cost devices for creating incisions in skin. For example, U.S. Pat. No. 5,851,215, issued on Dec. 22, 1998 to Mawhirt et al., teaches a low-cost safety lancet for creating a skin incision. The lancet contains a unitarily formed plastic body, thereby making the lancet device easy to manufacture at a low cost.

The lancet device includes a blade beam having a cutting blade disposed at one end for generating an incision in a patient's skin. U.S. Pat. No. 5,584,846, issued on Dec. 17, 1996 to Mawhirt et al., presents another low-cost safety lancet for creating a skin incision. The lancet contains a unitarily formed plastic body, containing a resilient spring loop that attaches an arm element to an opposing base element. A blade is disposed on the arm element.

Finally, a number of U.S. patents have issued in this field of art using an enclosed spring structure. For example, U.S. Pat. No. 4,064,871, issued on Dec. 27, 1977 to W. J. Reno, teaches a bleeding time testing device that includes a housing having a surface with a slot defining a longitudinal opening into the housing. A blade is mounted within the housing for movement of the blade tip through and along the slot. Biasing springs are provided within the housing to urge the blade through the slot a predetermined distance and along the slot for a predetermined length to control the depth and length of an incision produced with the device. A trigger is provided to initiate movement of the blade along with a safety pin to prevent the inadvertent activation of the device.

U.S. Pat. No. 5,314,441, issued on May 24, 1994 to Cusack et al., presents a lancet device with a blade support arm pivotably secured within a hollow housing. The pivot connection between the blade support arm and the housing is formed by a pivot pin, which is free to reciprocally move within the slot receptacle. The rotation of the blade support arm about the pivot pin is implemented by a bias spring. The blade of the device implements an incision and is again retracted into the housing traversing a "tear drop" shaped path.

U.S. Pat. No. 6,221,089, issued on Apr. 24, 2001 to Mawhirt et al., teaches a device for making an incision in skin, having a housing with a slotted opening, and a triggering mechanism disposed within the housing for propelling a blade coupled thereto, through the slotted opening of the housing to make an incision in the skin. The triggering mechanism includes a finger engageable trigger located external to the housing for actuating the triggering mechanism and a spring anchoring assembly for automated machine arming the device after the triggering mechanism has been assembled into the housing.

One of the problems associated with the use of the TRIPLETT™ device is that the force applied to actuate the device is off-center from the location at which the blade emerges from the cutting surface. As such, variations of pressures applied to the device can occur. As a result, the bleeding time testing can have a lack of consistent testing. Angular deflections of the cutting surface can also occur by the off-center application of pressure to the actuator of such cutting device. As such, a need has developed for a device for actuating such blood acquisition devices such that the pressure of actuation will be directly above the location of the incision.

U.S. Provisional Application Ser. No. 60/393,971, filed on Jul. 25, 2002, by the present applicant, describes a constant force actuator for a blood acquisition device. This constant force actuator is externally applied to an existing blood acquisition device. The blood acquisition device includes a body having a bottom surface from which a cutting blade can emerge so as to carry out an incision. The body includes a switch pin actuator that extends outwardly of the top surface in the acquisition device body. The switch pin is movable between a pre-actuating position and an actuating position. A safety tab is removably positioned between the switch pin actuator so as to retain the switch pin actuator in its pre-actuating position. The safety tab is to be removable so as to enable the testing device to be actuated by moving the switch pin from the pre-actuating position to the actuating position. The cutting blade is cooperative with the switch pin actuator to move outwardly of the bottom surface of the body of the testing device when the switch pin is moved to the actuating position.

In this provisional patent application, a constant force device is mechanically attached to the surface of the body of the blood acquisition device. The constant force device has a housing that is mounted onto the top surface of the blood acquisition device so as to extend parallel to the bottom surface of the device. A suitable spring clip is provided on the housing so as to allow the actuator housing to be affixed to the body of the blood acquisition device. A slide frame is mounted on the housing so as to be in slidable relationship to the housing. The slide frame is movable between a pre-activated position to an activated position. In the pre-activated position, the slide frame has a surface which resides against the switch pin actuator in the pre-activated position. A spring is mounted so as to be cooperative with the slide frame so as to urge the slide frame to the actuated position. An actuator button is slidably mounted on the housing so as to be slidable in a direction transverse to the plane of the bottom surface of the blood acquisition device. When the actuator button is depressed, the spring associated with the slide frame urges the slide frame in a horizontal direction parallel to the bottom surface of the blood acquisition device and thereby moves the switch pin actuator from the pre-actuating position to the actuating position. The actuator button is positioned directly above the center line of the cutting blade during the incision procedure.

It is an object of the present invention to provide a skin incision device that will not make the incision until a controlled vertical force is applied against the subject tissue.

It is another object of the present invention to provide a skin incision device that removes the variations of force that are applied by different operators at the time the incision is performed.

It is another object of the present invention to provide a skin incision device which allows the actuation force to be easily altered by a modification of an actuator means for the purpose of requiring different actuating forces to be provided.

It is a further object of the present invention to provide a skin incision device which can be assembled with no force required to load the components which interact to produce the incision.

It is a further object of the present invention to provide a skin incision device in which the blade is propelled by a designed controlled interaction of internal components which creates a slicing into, across and slicing out of subject tissue for the purpose of minimizing the trauma to the subject tissue.

It is a further object of the present invention to provide a skin incision device in which a consistent patterned incision can be made by the blade.

It is another object of the present invention to provide a skin incision device which reduces the introduction of undesirable components of the skin tissue into the incision area and blood sample.

It is still a further object of the present invention to provide a skin incision device that promotes rapid healing of the incision location.

It is still another object of the present invention to provide a skin incision device which has a concurrent action at the incision which locks the device and prohibits the ability of the device to be reloaded for additional uses.

It is a further object of the present invention to provide a device which is easy to use, relatively inexpensive and easy to manufacture.

These and other objections of the present invention will become apparent from a reading of the attached specification and appended claims.

BRIEF SUMMARY OF THE INVENTION

The present invention is a skin incision device that has a casing with a slot formed at a bottom surface thereof, a cover positioned on the casing and slidable in a direction transverse to a plane of the bottom surface of the casing, a blade pivotally positioned within the casing generally adjacent the slot, an actuator positioned within the casing, and a carriage anchored within the casing and pivotally attached to the blade. The actuator is actuatable by slidable movement of the cover toward the bottom surface of the casing and converts transverse movement of the cover into horizontal movement of the actuator. The horizontal movement of the actuator causes the actuator to engage the blade at a pre-actuated position through a post-actuated position such that at least a portion of the blade extends outwardly of the slot during the movement between the pre-actuated position and the post-actuated position. The carriage guides movement of the blade from the pre-actuated position through the post-actuated position.

In the present invention, the casing has a generally open end opposite the bottom surface and sides extending upwardly from the bottom surface and a top surface extending over the open end and over at least a portion of the sides of the casing. At least of one the sides of the casing has a barb extending outwardly therefrom. The cover has a wall extending over a portion of the side of the casing. The wall has a first retaining slot formed therein and a second retaining slot formed therein above the first retaining slot. The barb engages the first retaining slot when the blade is in the pre-actuated position. The barb engages the second retaining slot when the blade is in the post-actuated position.

The casing is further comprised of a release seat, a guide member, a capture seat and a lock member made integral with an inner surface of the casing. The release seat houses the actuator when the blade is in the pre-actuated position. The guide member has a bottom edge slidably contacting the carriage when the blade moves from the pre-actuated position to the post-actuated position. The capture seat retains the actuator at the post-actuated position. The lock member holds the actuator in the capture seat. The casing may be comprised of two portions that are joined together. One of the portions has an interior surface facing the interior surface of the other of the portions.

The blade of the present invention includes a razor member having a cutting edge, a retaining hole positioned on an end of the blade and an elongated hole positioned adjacent an opposite end of the blade. The elongated hole is rotatable relative to the casing. The carriage is cooperatively connected to the retaining hole so as to pivotally guide the razor member between the pre-actuated position and the post-actuated position. The casing has a blade retainer peg formed therein adjacent the slot of the casing such that the elongated hole of the blade is positioned on the blade retainer peg.

The blade can have a first pivot point interconnected to the casing and a second pivot point attached to the carriage. The first pivot point is in cam-relation/rotatable on the casing during movement of the blade from the pre-actuated position to the post-actuated position. The first pivot point of the blade can be an obround formed therein. This obround cam be positioned over a blade retainer peg of the casing.

In the present invention, the actuator includes a top edge, a resilient curved member extending downwardly from the top edge, and a knuckle positioned on a terminal end of the curved member. The top edge is in abutment with the inner surface of the cover during movement of the blade from the pre-actuated position to the post-actuated position. The knuckle is retained in position by the release seat when the blade is in the pre-actuated position and engages the blade during movement of the blade from the pre-actuated position to the post-actuated position. The casing retains the knuckle in the post-actuated position in the capture seat of the casing. Optionally, a lock member is used to prevent re-loading the actuator such that the present invention is a one-use applicator.

The carriage comprises an anchored end positioned in the casing, an arcuate member extending from the anchored end, and a cam positioned on a terminal end of a arcuate member and pivotally attached to the blade. The cam guides the movement of the blade outwardly from the slot and from the pre-actuated position and causes a horizontal movement of the blade after the outward movement, and guides another movement of the blade inwardly toward the slot and to the post-actuated position. The cam has a curved shape rotatable around a pivot point attached to the blade.

In general, the present invention is a device for making a standard incision in skin tissue for the purpose of blood acquisition. The present invention is a single-use/disposable device which includes the slot for the purpose of allowing the blade to travel out of the device to form the incision and then retracting back into the housing of the device. The movable cover travels in a downward motion so as to apply a constant pressure against the skin during actuation of the blade. The knuckle of the actuator will release from the release seat and contact the blade when a controlled load limit is achieved. When a controlled load limit is achieved, downward pressure of the cover is converted by the actuator into horizontal movement of the knuckle at an end of the actuator. The horizontal motion of the knuckle engages the blade at the pre-actuated position. As the knuckle moves horizontally, the blade is moved from the pre-actuated position to the post-actuated position. The carriage guides the blade during movement by the cam pivotally attached to the blade. The interaction of the surfaces of the cam against the guide member of the casing propels the razor member out of the housing, through the skin, and back into the housing in a very controlled action. This controlled action of the razor member is such the razor member is slicing upon entry into the skin, guided horizontally while at depth, and slicing upon exiting the skin. This action of slicing, both entering and exiting, will minimize the trauma to the skin, will reduce the introduction of undesirable elements of the skin tissue into the incision and blood sample, and will promote the rapid healing of the incision location.

DETAILED DESCRIPTION OF THE INVENTION

Figure 1:
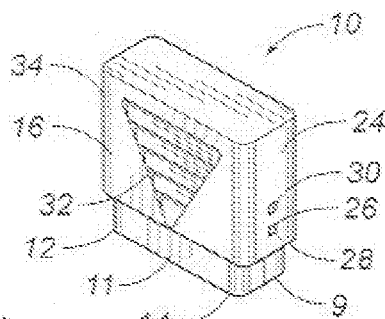
FIG. 1 is an outer perspective view of the skin incision device of the present invention.
Figure 2:
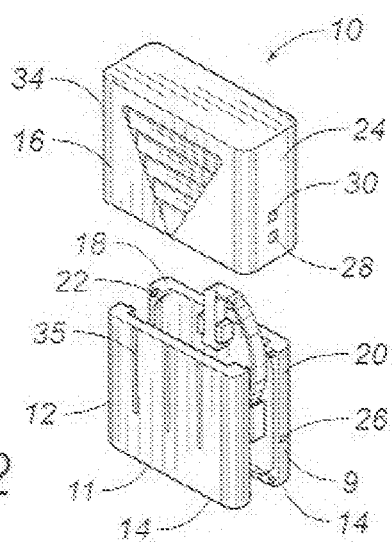
FIG. 2 is an exploded perspective view of the skin incision device showing the cover and the casing.

Referring to FIGS. 1 and 2, there is shown the skin incision device 10 in accordance with the teachings of the preferred embodiment of the present invention. The skin incision device 10 includes a casing 12 having a bottom surface 14 and a cover 16 slidably positioned on the casing 12. The top cover 16 is slidable in a direction transverse to a plane of the bottom surface 14. The casing 12 can have a first panel 9 and a second panel 11.

The casing 12 has a generally open end 18 opposite the bottom surface 14. The casing 12 has sides 20 and 22 extending upwardly from the bottom surface 14. The cover 16 extends over the open end 18 of the casing 12 and has a wall 24 extending over at least a portion of the side 20 of the casing 12. The side 20 has a barb 26 extending outwardly therefrom. The wall 24 has a first retaining slot 28 and second retaining slot 30 formed above the first retaining slot 28. As can be seen in FIG. 1, the barb 26 engages the first retaining slot 28.

In FIG. 1, the device 10 is shown in its pre-actuated position. Ultimately, the bottom surface 14 will be placed upon the surface of the skin and the cover 16 will be pressed downwardly toward the bottom surface 14. As a result, the barb 26 will free itself from the first retaining slot 28. When the device 10 has incised the skin and the blade is retained in its post-actuated position, the barb 26 will then be retained within the second retaining slot 30. As a result, the barb 26 prevents reuse of the device 10. Within the concept of the present invention and as shown in FIGS. 3–5, it is important to note that another barb 42 can also be placed on the opposite side 22 of casing 12 so as to suitably engage corresponding first retaining slot 37 and second retaining slot 39 formed on the opposite wall 34 of the cover 16.

In FIGS. 1 and 2, the cover 16 is also shown with triangularly shaped protrusions 32 that can be used for gripping the device 10. The triangular shape of the protrusions 32 further indicates the centerline of travel of the razor blade 38. The protrusions 32 may similarly be located on the opposite side of the cover 16. The casing 12 is also shown with a plurality of ridges 35 extending from the open end 18 of the casing 12. The ridges 35 may guide and align downward movement of the cover 16 along the casing 12. Cooperative structures along the interior surface of the cover 16 may engage the ridges 35 to align the casing 12.

Figure 3:
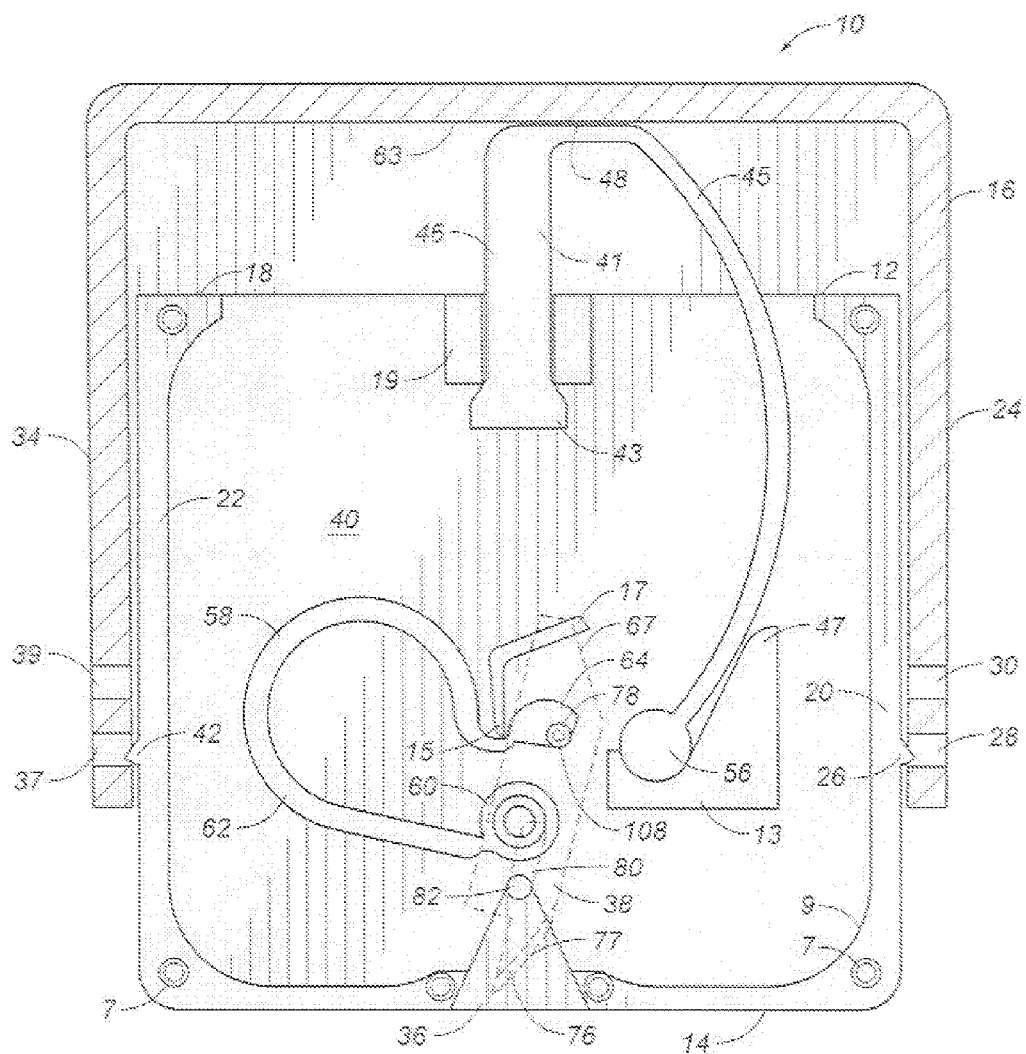
FIG. 3 is an interior elevation view of the interior structure of skin incision device of the present invention as shown in its pre-actuated position. The blade and cover are shown in broken lines.
Figure 4:
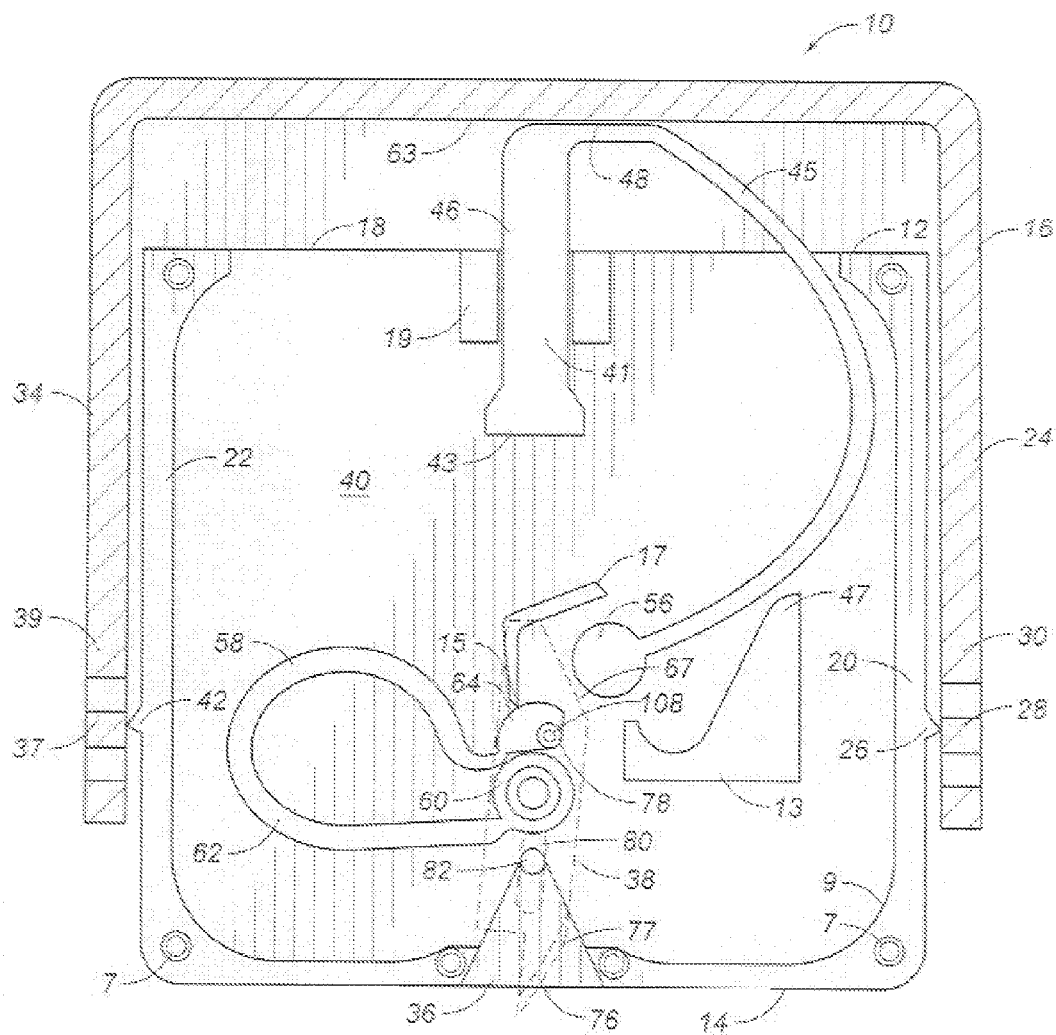
FIG. 4 is an interior elevation view of the interior structure of the skin incision device of the present invention showing the device in its movement between the pre-actuated position and the post-actuated position. The blade and cover are shown in broken lines.
Figure 5:
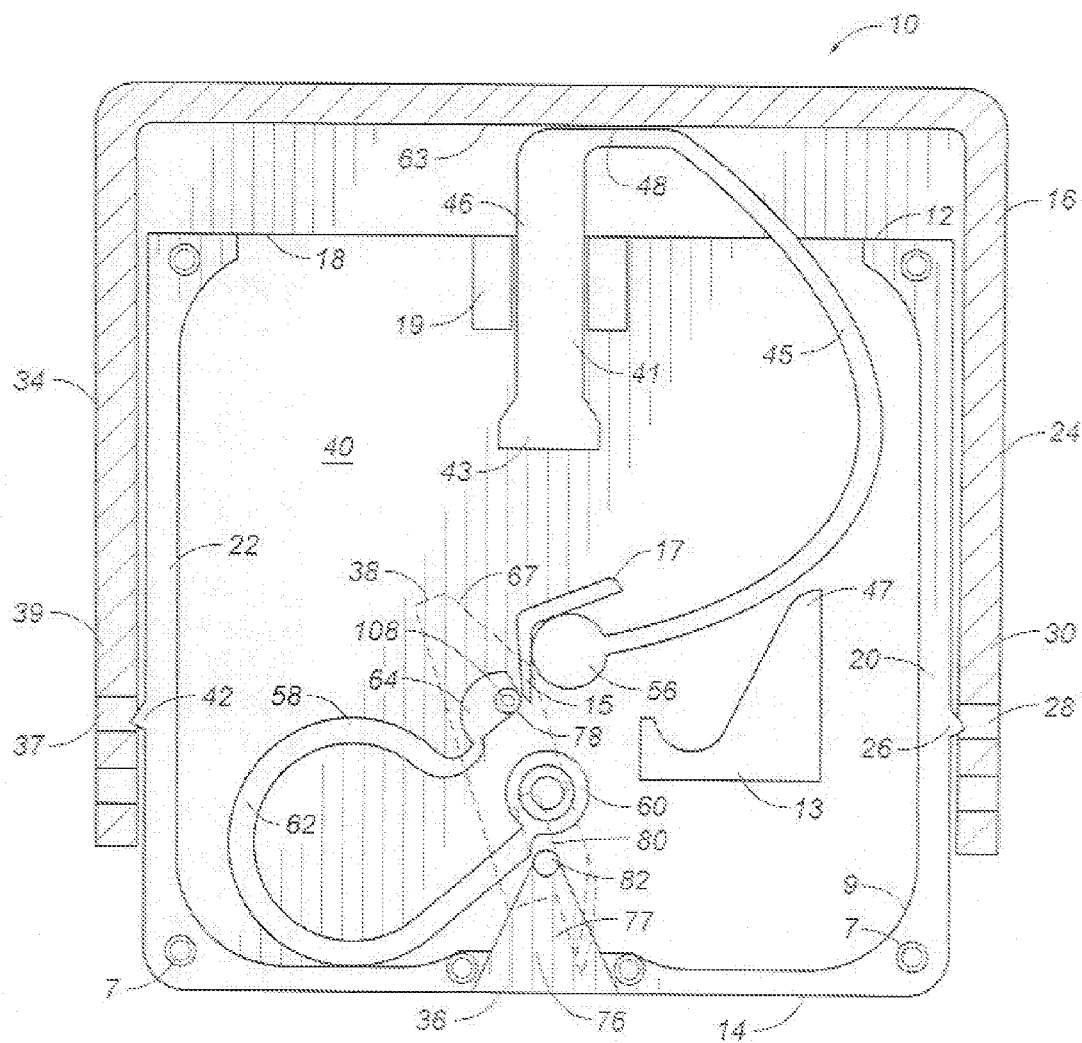
FIG. 5 is an interior elevation view of the interior structure of the skin incision device of the present invention showing the device in its post-actuated position within the first panel. The blade and cover are shown in broken lines. The knuckle rests in the knuckle travel pocket on the second panel in the post-actuated position (position in second panel not shown for post-actuated stage).
Figure 6:
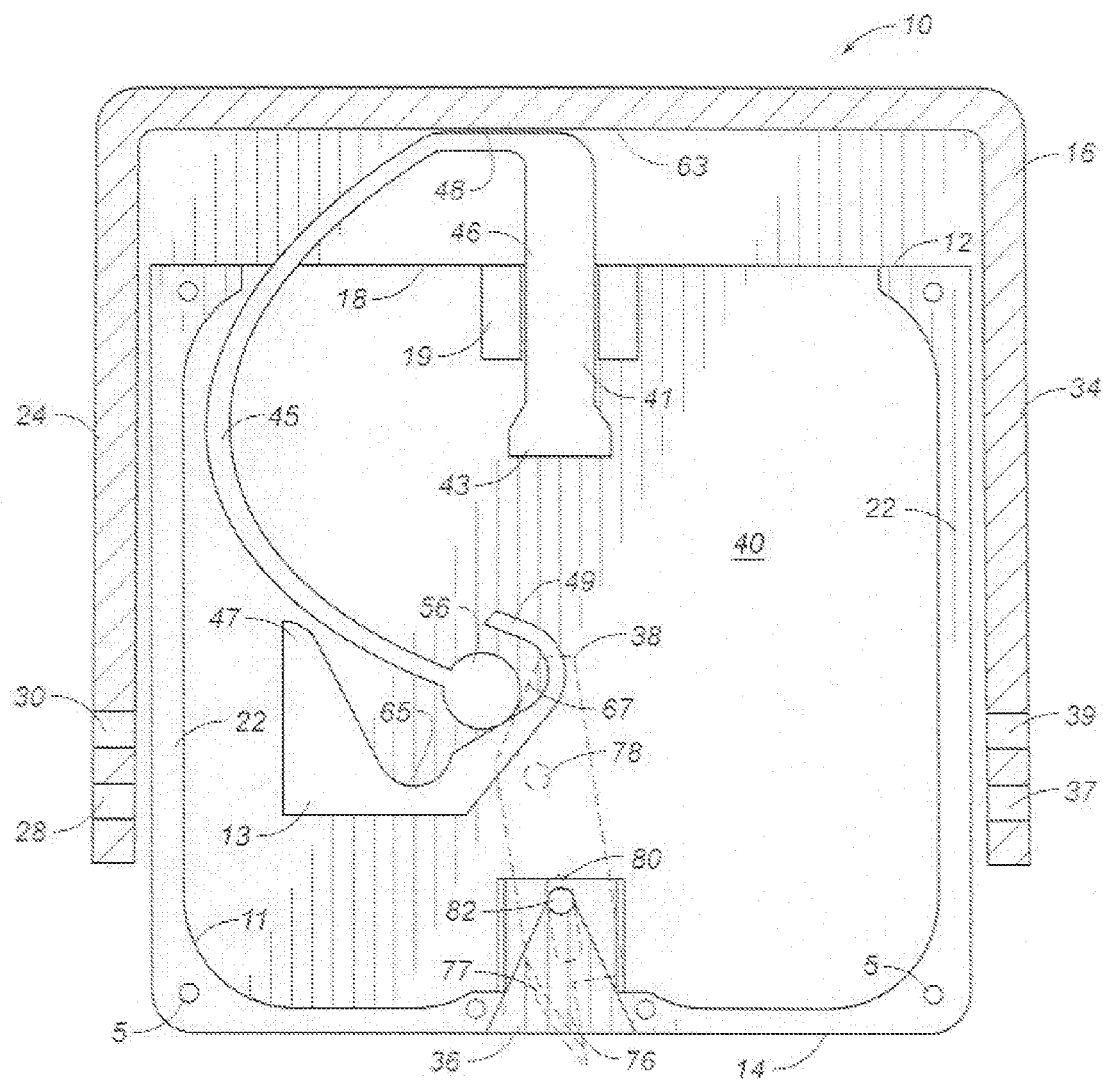
FIG. 6 is another interior elevation view of interior structure of the skin incision device of the present invention showing another panel of the casing shown in FIGS. 3–5. The blade and cover are shown in broken lines.

FIGS. 3–5 show the interior structure and working components of the device 10 of the present invention in sequential order from a pre-actuated position (FIG. 3), transition between positions (FIG. 4) and the post-actuated position (FIG. 5). Each of the FIGS. 3–5 show the blade 38, actuator 46 and carriage 58 of the present invention as positioned within the casing 12. FIGS. 3–5 show views of the first panel 9 of the casing 12, and FIG. 6 shows a view of the second panel 11 of the casing 12.

In particular, in the FIGS. 3–5, it can be seen that the casing 12 has a slot 36 formed on the bottom surface 14 thereof. A blade 38, indicated in broken lines, is positioned in the interior 40 of the casing 12 generally adjacent to the slot 36 and to the bottom surface 14. The casing 12 also has a side 20 extending upwardly from the bottom surface 14 and another side 22 extending upwardly from the bottom surface 14. A barb 26 is secured to the side 20 of casing 12. Another barb 42 is secured to the side 22 of casing 12. The cover 16 is shown in broken lines.

As can also be seen in FIG. 1, the barb 26 engages the first retaining slot 28 on the wall 24 of cover 16. The barb 42 engages a corresponding first retaining slot 37 formed on the wall 34 of the cover 16. As a result, the cover 16 will reside in its pre-actuated position.

In FIGS. 3–5, the casing 12 is presented with a release seat 13, a guide member 15, and a capture seat 17 all made integral with an inner surface of the casing 12. The release seat 13 retains the knuckle 56 of the actuator 46 when the blade 38 is in the pre-actuated position (FIG. 3). The guide member 15 is illustrated as a generally L-shaped member integral with the capture seat 17. However, the guide member 15 is actually the end surface of this L-shaped member, along which the surfaces of cam 64 contact. This end surface of guide member 15 slidably contacts the cam 64 of the carriage 58 when the blade 38 moves from the pre-actuated position to the post-actuated position (FIG. 4). The capture seat 17 retains the knuckle 56 of the actuator 46 at the post-actuated position (FIG. 5). The knuckle 56 of the actuator 46 is retained in the capture seat 17 so as to prevent re-setting the actuator 46 for more than one use. The cooperation of the barb 26 and retaining slot 30 and the barb 42 and retaining slot 39 also serves to prevent re-use. An alternative lock member may also be positioned within the interior 40 of the casing 12.

FIGS. 3–5 also show the casing 12 with a support member 19 made integral with an inner surface of the casing 12 and positioned adjacent the open end 18 of the casing 12. The support member 19 is in slidable contact with the stem 41 of the actuator 46 within the casing 12 during the transverse movement of the cover 16 when the blade 38 moves from the pre-actuated position to the post-actuated position. The support member 19 is in the form of a pair of parallel blocks arranged in parallel spaced relation. The stem has a bulbous head 43 at an end thereof so as to prevent outward movement of the stem 41 from the support member 19. This arrangement facilitates the installation and assembly of the actuator 46 within the casing 12. In particular, the actuator 46 can be installed in a pre-actuated configuration by way of the retention of the stem 41 in the support member 19.

As shown in FIG. 6, the skin incision device 10 of the present invention has a casing 12 comprised of a first panel 9 (shown in FIGS. 3–5) and a second panel 11 (FIG. 6) that are joined together. The second panel 11 fixably connects to the first panel 9 and defines the slot 36 between the first panel 9 and the second panel 11 at respective bottom surfaces 14 thereof. The structures of the casing 12 can be positioned on either first panel 9 or second panel 11, including barbs 26 and 42 on respective sides 20 and 22 thereof. The second panel 11 has pins 5 that are received within pin holes 7 of the first panel 9 so as to secure the panels 9 and 11 together and for a chamber or interior volume 40 therein. FIG. 6 shows the blade 38 in broken lines in the second casing 11 during horizontal movement from the pre-actuated position to the post-actuated position corresponding to the view of the first casing 9 in FIG. 4.

In FIGS. 3–5, it can also be seen that an actuator 46 has a top edge 48 cooperative with an inner surface 63 of the cover 16. The top edge 48 is in abutment with the inner surface 63 of the cover 16 during movement of the blade 38 from the pre-actuated position (FIG. 3) to the post-actuated position (FIG. 5). The actuator 46 has a resilient curved member 45 (in the form of a leaf spring) which will extend downwardly in a curved manner through the open end 18 of the casing 12. The terminal opposite end of the actuator 46 has knuckle 56 formed thereon. The actuator 46 can be suitably changed, replaced, altered, or otherwise manipulated so as to accommodate greater or lesser forces as required for the skin incision process. Typically, the thickness of the resilient curved member 45 and material selection of the actuator 46 will control the threshold amount of force to activate the blade 38.

The knuckle 56 is fixed by the casing 12 when the blade 38 is in the pre-actuated position at the release seat 13 shown in FIG. 3. The resilient member 45 will bend outwardly so as to contact an upper edge 47 of the release seat 13. This contact will cause the knuckle 56 to push upwardly and outwardly out of the notch 65 on the top surface of the release seat 13. The knuckle 56 contacts the blade 38 along edge 67 during movement of the blade 38 from the pre-actuated position to the post-actuated position shown in FIG. 4. Simultaneously and as shown in FIG. 6, there is a knuckle travel pocket 49 made integral with the second panel 11 of the casing 12. The knuckle travel pocket 49 guides the movement of the knuckle from the release seat 13 to the capture 17. The actuator 46 is prevented from interfering with other structures within the interior 40 by using the knuckle travel pocket 49 to stop extension of the knuckle 56 and resilient member 45 into the other structures in the casing 12, such as the cam 64. The casing 12 eventually retains the knuckle 56 in the post-actuated position at the capture seat 17 shown in FIG. 5.

The carriage 58 has a unique configuration within the casing 12. In particular, the carriage 58 has an anchored end 60 rotatably attached to the casing 12, an arcuate member 62 extending from the anchored end 60, and a cam 64 positioned on a terminal end of the arcuate member 62. The cam 64 is pivotally attached to the blade 38 at the pivot point 108 and guides the outward movement of the blade 38 from the slot 36 and from the pre-actuated position shown in FIG. 3. The cam 64 causes a horizontal movement of the blade 38 after the outward movement by slidably contacting a surface 104 of the cam 64 against the bottom surface of the guide member 15 of the casing 12, as shown in FIG. 4. The cam 64 also guides an inward movement of the blade 38 toward the slot 36 to the post-actuated position of FIG. 5. The arcuate member 62 may be a resilient member which springingly retracts the blade 38 vertically inward of the slot 36. The cam 64 typically has a curved shape rotatable around the pivot pin 108 attached to the blade 38.

Figure 7:
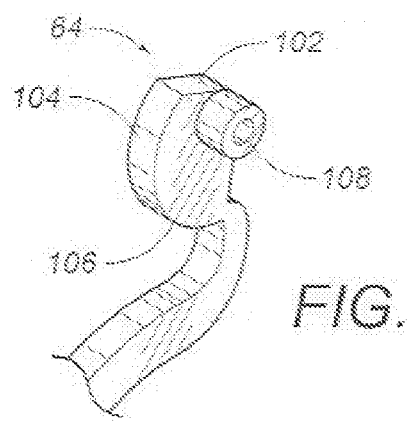
FIG. 7 is a partial enlarged perspective view of the cam of the carriage of the skin incision device of the present invention.

FIG. 7 shows a partial enlarged perspective view of the cam 64 of the carriage 58 of the skin incision device 10 of the present invention. The cam 64 is shown with the pivot pin 108 on an end of the cam 64 which is rotatably attached to the retaining hole 78 of the blade 38. The cam 64 has a flat back surface 106 which makes surface-to-surface contact with the guide member 15 in the pre-actuated position, a curved upper surface 104 corresponding to the travel path of the blade 38, and a flat forward surface 102 which pulls the cam 64 off the guide member 15 in the post-actuated position. As a result, the cam 64 pulls the blade 38 upward and prevents re-setting of the blade 38 in the pre-actuated position for more than one use. The flat forward surface 102 resides against the back of the guide member 15.

The blade 38 includes a razor member 76 having a cutting edge 77 formed at a lower end of the blade 38. Additionally, a retaining hole 78 is positioned adjacent an opposite end of the blade 38 such that the pivot pin 108 extending from the cam 64 of the carriage 58 is cooperatively received within the retaining hole 78. The carriage 58 pivotally guides the movement of the razor member 76 between the pre-actuated position and the post-actuated position. The blade 38 further comprises an elongated hole 80 positioned between the retaining hole 78 and the razor member 76 of the blade 38. The elongated hole 80 is rotatably attached to the casing 12 for anchoring the blade 38. The casing has a blade retainer peg 82 formed therein adjacent the slot 36 of the casing 12. The elongated hole 80 of the blade 38 is positioned on the blade retainer peg 82 such that the blade 38 is pivotally and slidably anchored to the casing 12. The elongated hole 80 may be of an obround shape in the blade 38 so as to be in generally pivotable and slidable relationship one the blade retainer peg 82.

The blade 38 also has a first pivot point at the elongated hole 80, which is connected to the casing 12 and a second pivot point at the retaining hole 78 attached to the carriage 58. At the first pivot point, the blade 38 is in cam-relation to the casing 12 and rotatable on the casing 12 during movement of the blade 38 from the pre-actuated position to the post-actuated position. The first pivot point of the blade 38 can also be an obround formed therein, the obround positioned over a blade retainer peg of the casing 12.

FIGS. 3–5 show the device 10 with blade 38 movement between the pre-actuated position and the post-actuated position in sequential order. In particular, in FIG. 3, it can be seen that the cover 16 is been pressed downwardly upon the casing 12. The inner surface 63 of the cover 16 contacts the top edge 48 of the actuator 46. As a result, the barbs 26 and 42 will be released from the respective first retaining slots 28 and 37 to be received within the respective second retaining slots 30 and 39 of the cover 16. The movable cover 16 travels in a downward motion and applies constant pressure against the skin during the actuation of the blade 38. The actuator 46 contacts the inner surface 63 of the cover 16 as it is actuated when a controlled load limit is achieved.

When a controlled load limit is achieved during the vertically downward pressure of the cover 16, it can be seen in FIG. 4 and FIG. 6 that the resilient member 45 of the actuator 46 becomes suitably compressed by the downward movement of the cover 16 relative to the bottom surface 14 of casing 12. The resilient curved portion of the actuator 46 will become distorted or distended such that the knuckle 56 is freed from the release seat 13 of the casing and is displaced horizontally from its pre-actuated position. FIG. 6 shows that the knuckle 56 upwardly pivots by cantilever action of the resilient member 45 having a fulcrum point at the upper edge 47 of the release seat 13. The actuator 46 has a lever action with the knuckle 56 at the end of the resilient member 45. The horizontal motion of the knuckle 56 engages the contact surface 67 of the blade 38 at the pre-actuated position. As the knuckle 56 moves horizontally in abutment to the contact surface 67 of the blade 38, the movement of the blade 38 is triggered from the pre-actuated position to the post-actuated position. In FIG. 6, the knuckle travel pocket 49 of the release seat 13 is also in surface-to-surface contact with the knuckle 56 so as to guide the movement of the knuckle 56. The resilient member 45 and the knuckle 56 are distended or distorted in a controlled path to prevent interference with other interior structures in the casing 12, such as the cam 64. The carriage 58 guides the blade 38 during movement by the cam 64 pivotally attached to the blade 38.

The interaction of the cam 64 against the guide member 15 of the casing 12 and the slidable contact by the elongated hole 80 of the blade 38 with the blade retainer peg 82 of the casing 12 propels the razor member 76 out of the casing 12, through the skin, and back into the casing 12 in a very controlled action. This controlled action of the blade 38 is such that the razor member 76 is slicing upon entry into the skin with the blade retainer peg 82 at one end of the elongated hole 80 and with the cam 64 at one end of its curved surface at the guide member 15 (FIG. 3). Then, the blade 38 is guided horizontally while at a set depth maintained by the blade retainer peg 82 sliding through to an opposite end of the elongated hole 80 and with the curved surface of the cam 64 and the guide 15 cooperatively maintaining the depth of the slice in the horizontal direction (FIG. 4). The vertical slicing of the blade 38 upon exiting the skin is accomplished by the resilient spring action of the arcuate member 62 of the carriage 58 as the cam 64 is released from the guide member 15 of the casing 12. The post-actuated position results in the blade retainer peg 82 being positioned in the original one end of the elongated hole 80 of the blade 38 (FIG. 5).

The controlled action of slicing, both entering and exiting, will minimize the trauma to the skin, will reduce the introduction of undesirable elements of the skin tissue into the incision and blood sample, and will promote the rapid healing of the incision location. The present invention creates a patterned incision by the outward movement of the blade 38, horizontal movement and inward movement of the blade. The patterned incision secures a more standard sample for analysis, unlike the prior art devices which rely upon a puncture or stabbing motion of the blade. Random tearing of the skin at the incision area and inconsistent depth of blade penetration are no longer factors which effect the sample analysis.

The operation of the present invention allows for a designed controlled force to be achieved. The cover 16 will travel vertically over the casing 12. The actuator 46 is restrained at one end by the support member 19 of the casing 12 and contacts the inner surface of cover 16. The opposite end of the actuator 46 is in contact with the release seat 13 of the casing 12. The cover 16 will continue to travel downwardly and the vertical application force is retained in the resilient curved member of the actuator 46 and converted to horizontal displacement of the knuckle 56. At a designed vertical pre-determined force, which is achieved as a function of distance traveled and resilient curved member flexing, the actuator 46 makes contact with the blade 38. The vertical pre-actuation force is released in a horizontal motion, as shown in FIGS. 3–5. This release is controlled by the strength of the leaf spring-like property of the resilient curved member 45.

The action described hereinbefore illustrates that a vertical force is appropriately transformed into a horizontal displacement on the interior of the casing 12. The knuckle 56 of actuator 46 will begin to travel in abutment against the blade 38. As the knuckle 56 travels horizontally against the blade 38, the movement of the blade 38 will be guided by the carriage 58, which is pivotally attached to the blade 38. In this encounter, the horizontal force will be converted to a outward vertical movement of the blade, a horizontal movement of the blade and an inward vertical movement of the blade. The interaction of the carriage 58, which is pivotally attached to the blade 38, with the guide member 15 of the casing 12 converts the horizontal force into the patterned movement of the blade 38. The curved surfaces of the cam 64 in cooperation with the guide member 15 and the elongated hole 80 of the blade in cooperation with the blade retainer peg 82 are uniquely designed to produce the patterned incision. Once the cam 64 of the carriage 58 begins to travel along its curve surface against the guide member 15, the blade 38 is forced to move vertically outward of the slot 36, then horizontally, and then vertically inward toward the slot 36 again. The inward vertical movement is determined by the release of spring action in the arcuate member of the carriage 58. A concurrent event also occurs at the same time. As described in previously, the barbs 26 and 42 will now engage the second retaining slots 30 and 39 on the walls 24 and 34 of the cover 16. As a result, the cover 16 will be restrained in a fixed condition which prohibits reuse of the device. Alternative lock members may also be positioned within the casing 12 so as to restrain the knuckle 56 in the capture seat 17 after use of the device.

The foregoing disclosure and description of the invention is illustrative and explanatory thereof. Various changes in the details of the illustrated construction can be made within the scope of the present invention without departing from the true spirit of the invention. The present invention should only be limited by the following claims and their legal equivalents.

We claim:

1. A skin incision device comprising:
    a casing having a slot formed at a bottom surface thereof, said bottom surface suitable for placement against the skin;
    a cover positioned over said casing, said cover being slidable in a direction transverse to a plane of said bottom surface of said casing;
    a blade pivotally positioned within said casing generally adjacent said slot, said blade having a pre-actuated position and a post-actuated position;
    an actuator means anchored to said casing, said actuator means being actuatable by slidable movement of said cover toward said bottom surface, said actuator means for converting transverse movement of said cover into horizontal movement of said actuator means, said actuator means engaging said blade at said pre-actuated position through said post-actuated position such that at least a portion of said blade extends outwardly of said slot during the movement between said pre-actuated position and said post-actuated position; and
    a carriage means anchored to said casing and pivotally attached to said blade, said carriage means for guiding movement of said blade from said pre-actuated position through said post-actuated position with a constant predetermined force of contact of said bottom surface of said casing with the skin regardless of a force applied to said cover.

2. The skin incision device of claim 1, said casing having a generally open end opposite said bottom surface, said casing having sides extending upwardly from said bottom surface.

3. The skin incision device of claim 2, at least one of said sides of said casing having a barb extending outwardly therefrom, said cover having a wall extending over a portion of the side of said casing, said wall having a first retaining slot formed therein and a second retaining slot formed therein above said first retaining slot, said barb engaging said first retaining slot when said blade is in said pre-actuated position, said barb engaging said second retaining slot when said blade is in post-actuated position.

4. The skin incision device of claim 1, wherein said casing is comprised of a release seat, a guide member, and a capture seat all made integral with an inner surface of said casing, said release seat retaining said actuator means when said blade is in said pre-actuated position, said guide member having a bottom edge slidably contacting said carriage means when said blade moves from said pre-actuated position to said post-actuated position, said capture seat receiving said actuator means at said post-actuated position.

5. The skin incision device of claim 1, wherein said casing comprises:
a first panel; and
a second panel fixedly connected to said first panel, said first and second panels defining said slot.

6. The skin incision device of claim 1, said blade comprising:
a razor member having a cutting edge;
a retaining hole positioned adjacent an end of said blade, said carriage means being cooperatively connected to said retaining hole so as to pivotally move said razor member between the pre-actuated position and the post-actuated position; and
an elongated hole positioned adjacent an opposite end of said blade, said elongated hole being rotatably interconnected to said casing.

7. The skin incision device of claim 6, said casing having a blade retainer peg formed therein adjacent said slot of said casing, said elongated hole of said blade positioned on said blade retainer peg.

8. A skin incision device comprising:
a casing having a slot formed at a bottom surface thereof, said casing having a retainer peg therein;
a cover positioned on said casing, said cover being slidable in a direction transverse to a plane of said bottom surface of said casing;
a blade pivotally positioned within said casing generally adjacent said slot, said blade having a pre-actuated position and a post-actuated position, said blade having a first pivot point connected to said casing, said first pivot point being an obround positioned over said retainer peg;
an actuator means anchored to said casing, said actuator means being actuatable by slidable movement of said cover toward said bottom surface, said actuator means for converting transverse movement of said cover into horizontal movement of said actuator means, said actuator means engaging said blade at said pre-actuated position through said post-actuated position such that at least a portion of said blade extends outwardly of said slot during the movement between said pre-actuated position and said post-actuated position, said blade having a second pivot point attached to said carriage means, said first pivot point being in rotatable and in cam relation to said casing during movement of said blade from said pre-actuated position to said post-actuated position; and
a carriage means anchored to said casing and pivotally attached to said blade, said carriage means for guiding movement of said blade from said pre-actuated position through said post-actuated position.

9. A skin incision device comprising:
a casing having a slot formed at a bottom surface thereof;
a cover positioned on said casing, said cover being slidable in a direction transverse to a plane of said bottom surface of said casing;
a blade pivotally positioned within said casing generally adjacent said slot, said blade having a pre-actuated position and a post-actuated position;
an actuator means anchored to said casing, said actuator means being actuatable by slidable movement of said cover toward said bottom surface, said actuator means for converting transverse movement of said cover into horizontal movement of said actuator means, said actuator means engaging said blade at said pre-actuated position through said post-actuated position such that at least a portion of said blade extends outwardly of said slot during the movement between said pre-actuated position and said post-actuated position
a carriage means anchored to said casing and pivotally attached to said blade, said carriage means for guiding movement of said blade from said pre-actuated position through said post-actuated position, said actuator means comprising:
a top edge in abutment with an inner surface of said cover during movement of said blade from said pre-actuated position to said post-actuated position;
a resilient curved member extending downwardly from said top edge; and
a knuckle positioned on a terminal end of said curved member, said knuckle being fixed by said casing and spaced from said blade when said blade is in said pre-actuated position, said knuckle contacting in blade during movement of said blade from said actuated position toward said post-actuated position.

10. The skin incision device of claim 9, wherein said casing retains said knuckle in said post-actuated position.

11. The skin incision device of claim 9, wherein said casing is further comprised of a knuckle travel pocket made integral with an inner surface of said casing.

12. The skin incision device of claim 9, wherein said casing is comprised of a support member made integral with an inner surface of said casing and positioned adjacent a top surface of said casing, said support member in slidable contact with said actuator means within said casing during said transverse movement of said cover.

13. A skin incision device comprising:
a casing having a slot formed at a bottom surface thereof;
a cover positioned on said casing, said cover being slidable in a direction transverse to a plane of said bottom surface of said casing;
a blade pivotally positioned within said casing generally adjacent said slot, said blade having a pre-actuated position and a post-actuated position;
an actuator means anchored to said casing, said actuator means being actuatable by slidable movement of said cover toward said bottom surface, said actuator means for converting transverse movement of said cover into horizontal movement of said actuator means, said actuator means engaging said blade at said pre-actuated position through said post-actuated position such that at least a portion of said blade extends outwardly of said slot during the movement between said pre-actuated position and said post-actuated position; and
a carriage means anchored to said casing and pivotally attached to said blade, said carriage means for guiding movement of said blade from said pre-actuated position through said post-actuated position, said carriage means comprising:
- an anchored end connected to said casing;
- an arcuate member extending from said anchored end; and
- a cam means positioned on a terminal end of said arcuate member and pivotally attached to said blade, said cam means for guiding outward movement of said blade through said slot and for causing a horizontal movement of said blade after said outward movement and for guiding an inward movement through said slot.

14. The skin incision device of claim 13, wherein said cam means has a curved shape rotatable around a pivot point attached to said blade.

15. A skin incision device comprising:
- a casing having a slot formed at a bottom surface thereof;
- a cover positioned over said casing, said cover being slidable in a direction transverse to a plane of said bottom surface of said casing;
- a blade pivotally positioned within said casing generally adjacent said slot, said blade having a pre-actuated position and a post-actuated position;
- an actuator having an end cooperative with an inner surface of said cover and extending downwardly into said casing; and
- a carriage means positioned within said casing and pivotally attached to said blade, said actuator cooperative with said blade from said pre-actuated position to said post-actuated position, said carriage means moveable within said casing for guiding said blade between said pre-actuated position and said post-actuated position, said actuator being comprised of a resilient member having a knuckle formed at an end of said resilient member, said knuckle being spaced from said blade at said pre-actuated position, said knuckle contacting said blade during movement between said pre-actuated position toward said post-actuated position.

16. The skin incision device of claim 15, said carriage means comprising:
- an arcuate member with an anchored end rotatably fastened to said casing; and
- a cam surface formed on a terminal end of said arcuate member and pivotally attached to said blade, said cam surface cooperative with said casing during an outward movement of said blade through said slot from said pre-actuated position and during a horizontal movement of said blade after said outward movement and during an inward movement through said slot to said post-actuated position.

17. The device of claim 15, said casing having a blade retainer peg formed therein, said blade comprising:
- a razor member having a cutting edge;
- a retaining hole positioned adjacent an end of said blade, said carriage means being cooperatively connected to said retaining hole so as to pivotally move said razor member between the pre-actuated position and the post-actuated position; and
- an elongated hole positioned adjacent an opposite end of said blade, said elongated hole being rotatably mounted on said blade retainer peg of said casing.

* * * * *